US00PP25795P2

(12) United States Plant Patent
Wood

(10) Patent No.: US PP25,795 P2
(45) Date of Patent: Aug. 11, 2015

(54) ***HYPERICUM* PLANT NAMED 'SMHKBF'**

(50) Latin Name: *Hypericum kalmianum*
Varietal Denomination: SMHKBF

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 71 days.

(21) Appl. No.: 13/998,224

(22) Filed: Oct. 11, 2013

(51) Int. Cl.
*A01H 5/00* (2006.01)

(52) U.S. Cl.
USPC ..... Plt./226

(58) Field of Classification Search
USPC ..... Plt./226
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hypericum* plant named 'SMHKBF', characterized by its compact and uniformly low mounding plant habit; blue-colored leaves; freely flowering habit; bright yellow-colored flowers; and good garden performance.

2 Drawing Sheets

Botanical designation: *Hypericum kalmianum.*
Cultivar denomination: 'SMHKBF'.

BACKGROUND OF THE INVENTION

The present invention relates to a new and distinct *Hypericum* plant, botanically known as *Hypericum kalmianum* and hereinafter referred to by the name 'SMHKBF'.

The new *Hypericum* plant is a product of a planned breeding program conducted by the Inventor in Grand Haven, Mich. The objective of the breeding program is to create new compact *Hypericum* plants with uniform plant habit and unique leaf color.

The new *Hypericum* plant originated from an open-pollination during the summer of 2007 in Grand Haven, Mich. of *Hypericum kalmianum* 'Very Blue', not patented, as the female, or seed parent with an unknown selection of *Hypericum kalmianum,* as the male, or pollen, parent. The new *Hypericum* plant was discovered and selected by the Inventor as a single flowering plant within the progeny of the stated open-pollination in a controlled environment in Grand Haven, Mich. in early 2009.

Asexual reproduction of the new *Hypericum* plant by softwood cuttings in Grand Haven, Mich., since the June, 2009 has shown that the unique features of this new *Hypericum* plant are stable and reproduced true to type in successive generations.

SUMMARY OF THE INVENTION

Plants of the new *Hypericum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHKBF'. These characteristics in combination distinguish 'SMHKBF' as a new and distinct *Hypericum* plant:

1. Compact and uniformly low mounding plant habit.
2. Blue-colored leaves.
3. Freely flowering habit.
4. Bright yellow-colored flowers.
5. Good garden performance.

Plants of the new *Hypericum* differ from plants of the female parent, 'Very Blue', in the following characteristics:

1. Plants of the new *Hypericum* are more compact than plants of 'Very Blue'.
2. Plants of the new *Hypericum* are more uniform than plants of 'Very Blue'.
3. Plants of the new *Hypericum* are more freely flowering than plants of 'Very Blue'.

Plants of the new *Hypericum* can also be compared to plants of *Hypericum* 'Bleu Velvet', not patented. In side-by-side comparisons conducted in Grand Haven, Mich., plants of the new *Hypericum* differed primarily from plants of 'Bleu Velvet' in plant habit as plants of the new *Hypericum* were shorter than plants of 'Bleu Velvet'. In addition, leaf color of plants of the new *Hypericum* was brighter blue than leaf color of plants of 'Bleu Velvet'.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet comprises a side perspective view of a typical flowering plant of 'SMHKBF' grown in a container.

The photograph on the second sheet is a close-up view of a typical flowering plant of 'SMHKBF'.

DETAILED BOTANICAL DESCRIPTION

The aforementioned photographs and following observations, measurements and values describe plants grown during the summer in three-gallon containers in an outdoor nursery in Grand Haven, Mich. and under commercial practices typical of commercial production. Plants were three years old when the photographs and description were taken. In the following description, color references are made to The Royal Horticultural Society Colour Chart, 1995 Edition, except where general terms of ordinary dictionary significance are used.

Botanical classification: *Hypericum kalmianum* 'SMHKBF'.

Parentage:

*Female, or seed, parent.*—*Hypericum kalmianum* 'Very Blue', not patented.

*Male, or pollen, parent.*—Unknown selection of *Hypericum kalmianum,* not patented.

Propagation:

*Type cutting.*—Softwood cuttings.

*Time to initiate roots.*—About 30 days at 24° C.

*Time to produce a rooted young plant.*—About four months at 24° C.

*Root description.*—Fine, fibrous; white and brown in color.

*Rooting habit.*—Freely branching; dense.

Plant description:

*Plant and growth habit.*—Compact and uniformly low mounding plant form; freely branching habit with about 47 lateral branches developing per plant; dense and bushy plant form; vigorous growth habit.

*Plant height.*—About 35 cm.

*Plant width* (*spread*).—About 65 cm.

*Lateral branch description.*—Length: About 31 cm. Diameter: About 2 mm. Internode length: About 2 cm. Strength: Strong. Aspect: Erect to about 20° from vertical. Texture: Smooth, glabrous. Color: Close to 200C.

Leaf description:

*Arrangement.*—Opposite, simple.

*Length.*—About 3.2 cm.

*Width.*—About 6 mm.

*Shape.*—Lanceolate.

*Apex.*—Acute.

*Base.*—Attenuate.

*Margin.*—Entire.

*Texture, upper and lower surfaces.*—Smooth, glabrous.

*Venation pattern.*—Pinnate.

*Color.*—Developing leaves, upper surface: Close to 135A and 189B. Developing leaves, lower surface: Close to 137C. Fully expanded leaves, upper surface: Close to 189B and 122A; venation, close to 198C. Fully expanded leaves, lower surface: Close to 189B and 122A; venation, close to 189A.

*Petioles.*—Length: About 3 mm. Width: About 2 mm. Texture, upper and lower surfaces: Smooth, glabrous. Color, upper and lower surfaces: Close to 138D.

Flower description:

*Flower form and arrangement.*—Single star-shaped flowers arranged in terminal clusters; freely flowering habit with about 21 flowers developing per lateral branch; flowers face mostly upright to outwardly.

*Fragrance.*—None detected.

*Natural flowering season.*—Plants of the new *Hypericum* typically flower from late June to late July in Michigan; flowers not persistent.

*Flower buds.*—Length: About 6 mm. Diameter: About 4 mm. Shape: Ovate to rounded. Color: Close to 143C.

*Flower diameter.*—About 2.5 cm.

*Flower depth* (*height*).—About 1.5 cm.

*Petals.*—Quantity and arrangement: Five in a single whorl. Length: About 1 cm. Width: About 6 mm. Shape: Elliptic. Apex: Obtuse. Base: Attenuate. Margin: Entire. Texture, upper and lower surfaces: Smooth, glabrous. Color: When opening, upper surface: Close to 5B. When opening, lower surface: Close to 6C. Fully opened, upper surface: Close to 5A; color becoming closer to 17B with development. Fully opened, lower surface: Close to 6C.

*Sepals.*—Quantity and arrangement: Five in a single whorl. Length: About 1.4 cm. Width: About 3 mm. Shape: Lanceolate. Apex: Acute. Base: Attenuate. Margin: Entire. Texture, upper and lower surfaces: Smooth, glabrous. Color: When opening and fully opened, upper surface: Close to 136A. When opening and fully opened, lower surface: Close to 137B.

*Peduncles.*—Length: About 1.4 cm. Diameter: About 2 mm. Strength: Strong. Aspect: About 30° to 50° from lateral branch axis. Texture: Smooth, glabrous. Color: Close to 144B.

*Reproductive organs.*—Stamens: Quantity per flower: About 142. Anther length: About 0.5 mm. Anther shape: Rounded. Anther color: Close to 34B. Pollen amount: Abundant. Pollen color: Close to 12A. Pistils: Quantity per flower: Three. Pistil length: About 1.1 cm. Stigma shape: Pointed. Stigma color: Close to 151B. Style length: About 1.1 cm. Style color: Close to 151B. Ovary color: Close to 151B.

*Seeds and fruits.*—Seed and fruit development have not been observed on plants of the new *Hypericum.*

Disease & pest resistance: Plants of the new *Hypericum* have not been noted to be resistant to pathogens and pests common to *Hypericum* plants.

Garden performance: Plants of the new *Hypericum* have exhibited good garden performance tolerating rain, wind and temperatures ranging from about −25° C. to about 35° C.

It is claimed:

1. A new and distinct *Hypericum* plant named 'SMHKBF' as illustrated and described.

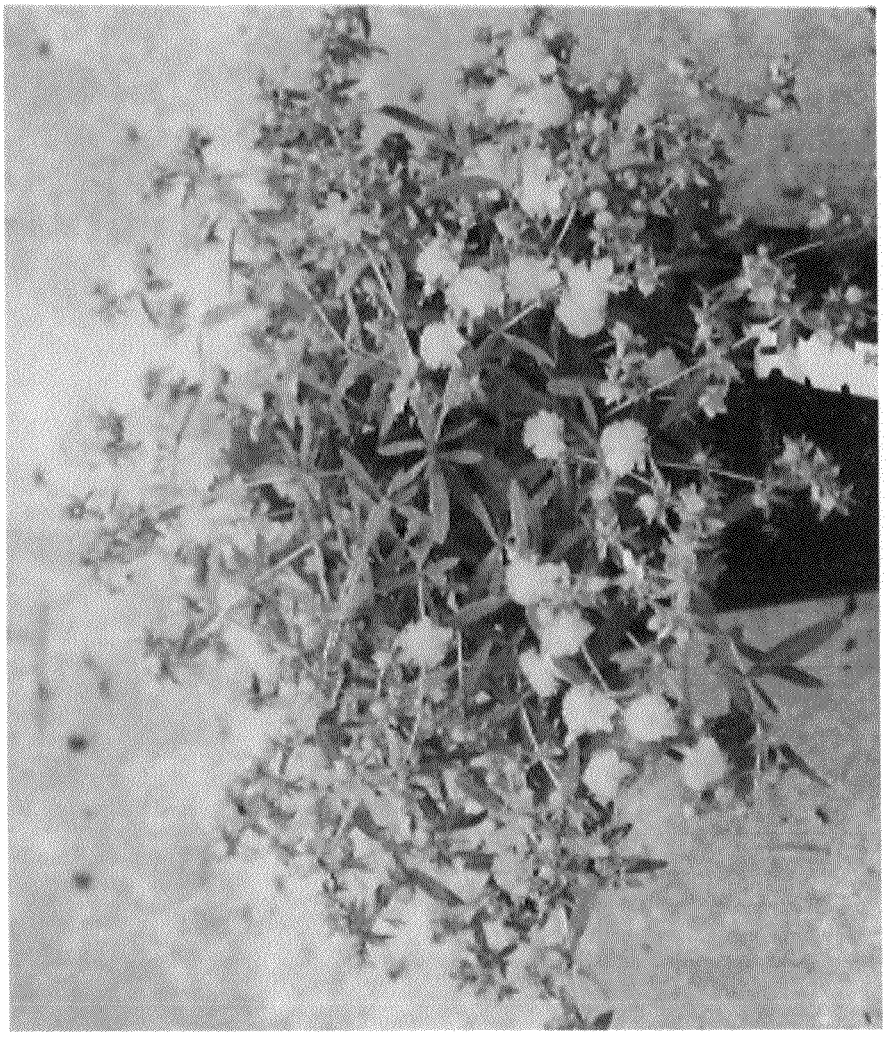

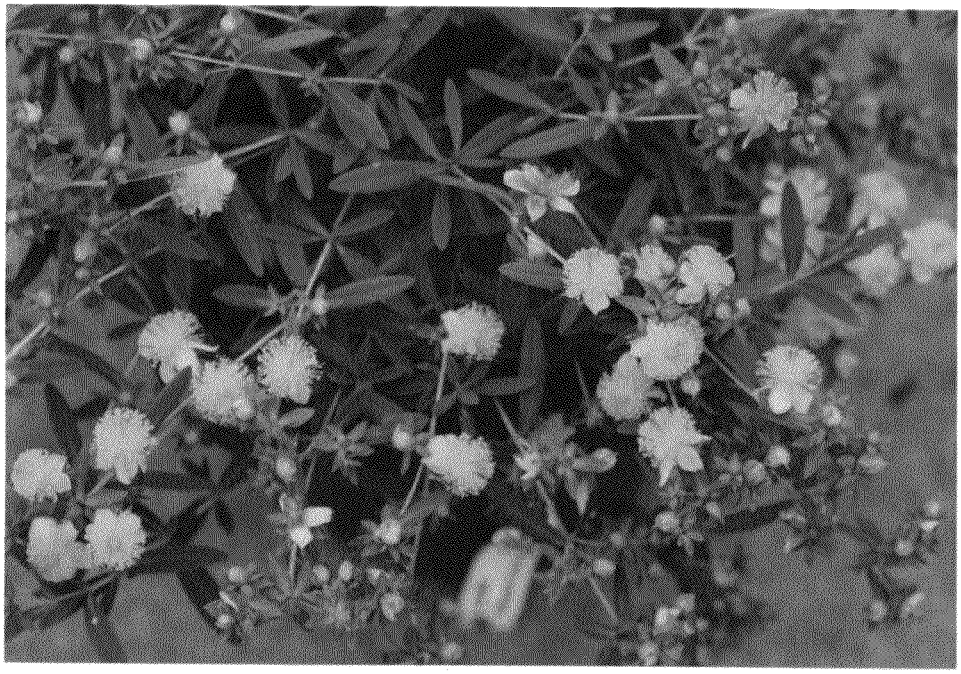

* * * * *